United States Patent [19]
Wong et al.

[11] Patent Number: 5,876,981
[45] Date of Patent: Mar. 2, 1999

[54] TRANSGLYCOSYLATION REACTIONS EMPLOYING β-GALACTOSIDASE

[75] Inventors: Chi-Huey Wong, Rancho Santa Fe; Teiji Kimura, San Diego, both of Calif.

[73] Assignee: The Scripps Research Institute, La Jolla, Calif.

[21] Appl. No.: 733,232

[22] Filed: Oct. 17, 1996

[51] Int. Cl.[6] ............ C12P 19/14; C12P 19/18; C12P 19/04; C12N 9/38
[52] U.S. Cl. ............ 435/99; 435/97; 435/100; 435/101; 435/74; 435/207; 536/17.8
[58] Field of Search .................. 435/100, 101, 435/99, 74, 207, 97; 536/17.8

[56] References Cited

U.S. PATENT DOCUMENTS

| | | | |
|---|---|---|---|
| 5,104,797 | 4/1992 | Mazur et al. | 435/105 |
| 5,532,147 | 7/1996 | Nilsson | 435/100 |

FOREIGN PATENT DOCUMENTS

| | | | |
|---|---|---|---|
| 0551107 | 7/1993 | European Pat. Off. | C12P 19/14 |

OTHER PUBLICATIONS

Chemical Abstracts 119(17):179341n, 1993.
Angew. Chem., Int'l Ed. 35(20):2348–2350, 1996.
Lee et al, Anal. Biohem. 216:358–364, 1994.
Toone et al, Tetrahedron 45(17):5397–5405, 1989.

*Primary Examiner*—Francisco Prats
*Attorney, Agent, or Firm*—Donald G. Lewis

[57] ABSTRACT

β-Galactosides are synthesized using a transglycosylation reaction catalyzed by β-galactosidase. The reaction employs a carbohydrate donor having a glycosidic leaving group attached to its anomeric carbon and an oxo group attached to the C-6 carbon. Strong leaving groups are preferred over weak leaving groups. The method can be carried out in aqueous solution without organic solvents to give the transglycosylation product in high yields and high regioselectivity. The synthesis of lactosamine using this methodology with galactose oxidase (GO) and β-galactosidase has been accomplished. (FIG. 3). The methodology affords simple reaction conditions and minimal purification steps. In addition, the intermediate substrates maintain high stability, the process affords high yields and the enzymes and reagents employed are commercially available with high stability and low costs.

14 Claims, 4 Drawing Sheets

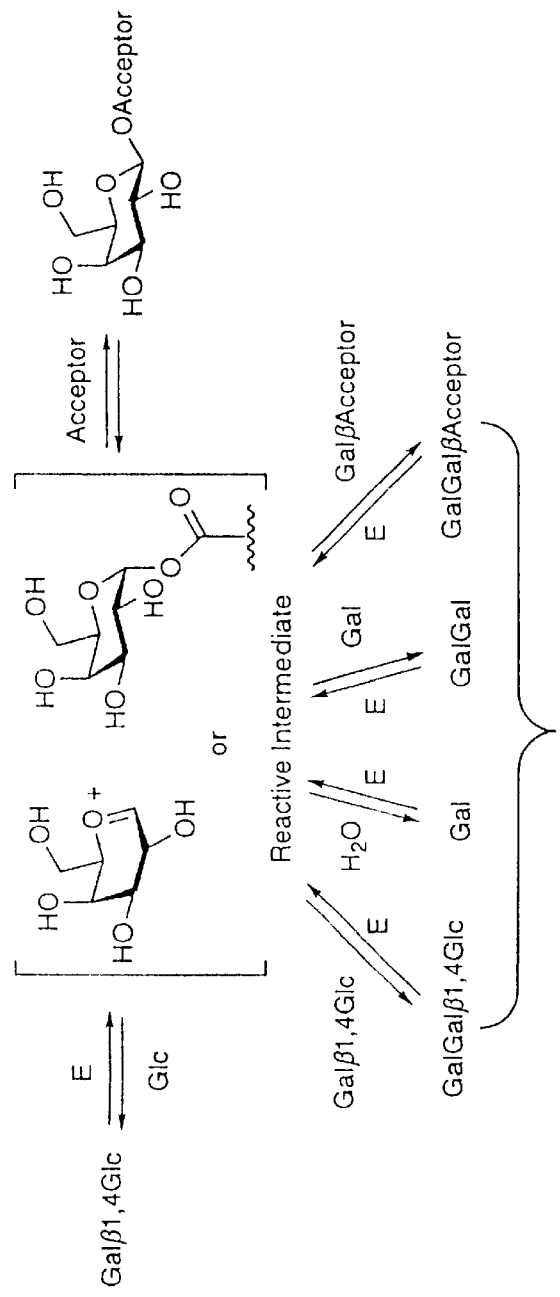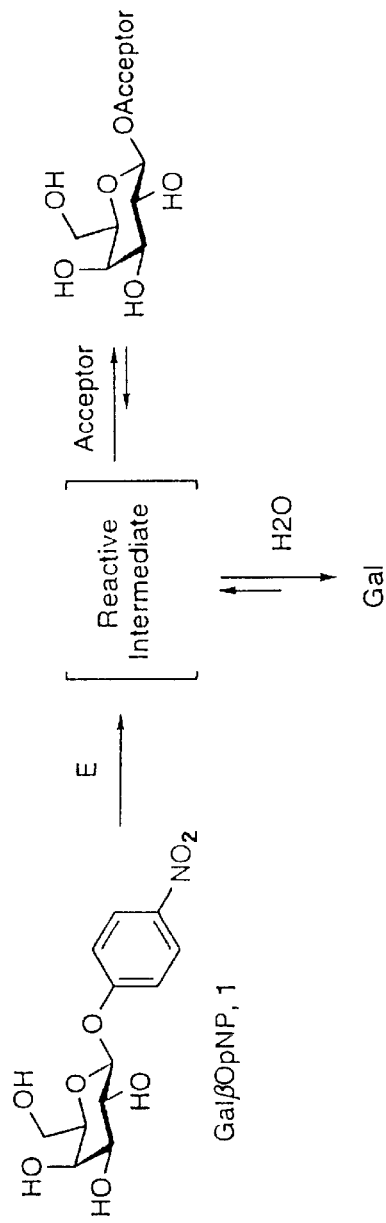
FIG. 1(a)
FIG. 1(b)

| entry[a] | Donor | Concentration of Acceptor (M) | $[V]_0$[b] (mM/min) | Yield of LacNAc (%) |
| --- | --- | --- | --- | --- |
| 1 | GalβOpNP (1) | 0 | 5.69±0.11 | |
| 2 | GalβOpNP (1) | 0.05 | 4.68±0.08 | 14 |
| 3 | GalβOpNP (1) | 0.5 | 4.16±0.23 | 30 |
| 4 | 6-oxo-GalβOpNP (2) | 0 | 0.074±0.008 | |
| 5 | 6-oxo-GalβOpNP (2) | 0.05 | 0.137±0.006 | 29[c] |
| 6 | 6-oxo-GalβOpNP (2) | 0.5 | 0.393±0.013 | 60[c] |

FIG. 2

TRANSGLYCOSYLATION REACTIONS EMPLOYING β-GALACTOSIDASE

GOVERNMENT RIGHTS

This invention was made with government support under Grant No. GM 44154 awarded by the National Institutes of Health. The U.S. government has certain rights in the invention.

TECHNICAL FIELD OF THE INVENTION

The present invention relates to transglycosylation reactions employing β-galactosidase. More particularly, the present invention relates to methods for enhancing the yield and regioselectivity of β-galactosidase catalyzed transglycosylation reactions.

BACKGROUND OF THE INVENTION

A recent expansion of our understanding of the biological role and clinical utility of oligosaccharides has created a need for new synthetic methodologies for inexpensively producing large quantities of these compounds. (Lowe et al. *Cell* 1990, 63, 475–484; Feizi et al., *Trends Biochem. Sci.* 1991, 16, 84–86) β-Galactosides are an important class of oligosaccharide for which many new bioactivities have recently been characterized and for which new synthetic methodologies are needed. For example, N-acetyl-D-lactosamine (LacNAc or Galβ1,4GlcNAc) has been determined to have clinical utility with respect to cellular recognition processes. (Feizi et al. *Biochemistry* 1994, 33, 6342–6349; Liu et al., *Immunol. Today* 1993, 14, 486–490; Sparrow et al. *J. Biol. Chem.* 1987, 262, 7383–7390.) Conventional methodologies for synthesizing N-acetyl-D-lactosamine are inadequate for commercial application.

For example, conventional synthetic methodologies from organic chemistry may be employed for producing N-acetyl-D-lactosamine. (Toshima et al. *Chem. Rev.* 1993, 93, 150314 1531; Schmidt et al., *Angew. Chem. Int. Ed. Engl.* 1986, 25, 212–235; Paulsen et al., ibid. 1982, 21, 155–173; Sinay et al., *Pure Appl. Chem.* 1991, 63, 519–528; Paulsen et al., *Angew. Chem., Int. Ed. Engl.* 1990, 29, 823–839). However, these conventional organic methodologies are complex and involve many steps and undesired side reactions.

When enzymatic methodologies are available for synthesizing oligosaccharides, they are often preferred over organic methodologies. As compared to chemical methodologies, many enzymatic methodologies are characterized by their relative simplicity and absence of side reactions. For example, N-acetyl-D-lactosamine (LacNAc) may be enzymatically synthesized using either β1,4-glycosyltransferase or β-galactosidase.

In the β1,4-glycosyltransferase-catalyzed reaction, a glycosyl group is transferred from a donor, e.g. UDP-galactose, to an acceptor saccharide to form the disaccharide N-acetyl-D-lactosamine (LacNAc). In an improved version of the β1,4-glycosyltransferase-catalyzed reaction, the UDP-galactose donor is regenerated in situ. (Ichikawa et al. *J. Am. Chem. Soc.* 1992, 114, 9283–9298.) The process gives high regioselectivity and yield, but the limited availability of the enzymes and their high cost and instability have hampered their use in large scale synthesis (Augé et al. *Carbohydr. Res.* 1990, 200, 257–268).

β-Galactosidase is an enzyme which, in its preferred direction, hydrolyzes glycosidic bonds, i.e., a glycosyl group is transferred from a donor glycoside or oligosaccharide to water. However, at high substrate concentrations, the reverse glycosyl transfer reaction may occur, viz., β-galactosidase may be employed for catalyzing transglycosylation reactions. The advantages of the galactosidase-catalyzed reaction are the enzyme's low cost, high stability and simple reaction conditions, i.e., there is no need for sugar nucleotides. (David et al. *Chemtracts-Org. Chem.* 1994, 7, 92–95; Takayama et al. *Bioorg. Med. Chem. Lett.* in press.) There are, however, some disadvantages associated with the use of galactosidase-catalyzed reactions. Because of the hydrolytic nature of the enzyme, the yields hitherto reported have been low and the desired compound was difficult to isolate from reaction mixtures containing quite similar products. (Usui et al. *Carbohydr. Res.* 1993, 244, 315–323; Herrmann et al. *Angew. Chem. Int. Ed. Engl.* 1993, 32, 1342–1343; Herrmann et al. *Tetrahedron Lett.* 1993, 34, 3091–3094.)

For representative examples of other glycosidase-catalyzed synthesis, see Nilsson et al. *Trends Biotechnol.* 1988, 6, 256–264; Crout et al. *Pure Appl. Chem.* 1992, 64, 1079–1084; Lehmann et al. *Carbohydr. Res.* 1979, 71, 65–73; Gais et al., Zeissler et al *Tetrahedron Lett.* 1988, 29, 5743–5744; Sauerbrei et al., Thiem et al., *Tetrahedron Lett.* 1992, 33, 201–204; Kobayashi et al. *J. Am. Chem. Soc.* 1991, 113, 3079–3084; López et al. *J. Org. Chem.* 1994, 59, 737–745; Petit et al. *Tetrahedron Lett.* 1991, 32, 6125–6128; David et al., *Chemtracts-Org. Chem.* 1994, 7, 92–95; Takayama et al., Shimazaki et al., *Bioorg. Med. Chem. Lett.* in press; Ajisaka, et al. *Carbohydr. Res.* 1994, 259, 103–115.

Substrate specificities can limit the applicability of enzymatic methodologies. The limitations introduced by substrate specificities may sometimes be partially overcome by chemically modifying the substrate. Accordingly, chemo-enzymatic methodologies can have an expanded synthetic scope as compared to purely enzymatic methodologies.

What is needed is a method for synthesizing β-galactosides in high yield and without significant side reactions using a transglycosylation reaction catalyzed by β-galactosidase.

SUMMARY

The invention is directed to a method for synthesizing β-galactosides using a transglycosylation reaction catalyzed by β-galactosidase. The reaction employs a carbohydrate donor having a glycosidic leaving group attached to its anomeric carbon and an oxo group attached to the C-6 carbon. Strong leaving groups are preferred over weak leaving groups. The C-6 oxo group promotes the efficiency of the β-galactosidase catalyzed transglycosylation reaction. The strong leaving group reduces the number of side reactions.

One aspect of the invention is directed to an improved process for producing a transglycosylation product. The process employs a galactosidase for catalyzing a transglycosylation reaction between a first galactosidase substrate and a second galactosidase substrate for producing the transglycosylation product. The first substrate is a carbohydrate donor having an anomeric carbon and a C-6 carbon. The anomeric carbon has a glycosidic leaving group attached thereto. The second substrate is a glycosyl acceptor. The improvement is characterized by the attachment of an oxo group to the C-6 carbon of the carbohydrate donor. The attachment of the oxo group to the C-6 carbon of the carbohydrate donor has the effect to greatly enhancing the efficiency of the transglycosylation reaction. A preferred first galactosidase substrate is represented by the following formula:

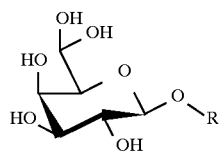

wherein R is selected from a group consisting of radicals represented by the following structures:

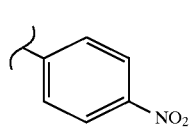 and 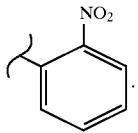

The oxo group may be an equilibrium between an aldehyde form and a diol form.

The oxo group may be attached to the C-6 carbon of the carbohydrate donor prior to the catalyzation of the transglycosylation reaction by oxidizing a precursor carbohydrate donor. The precursor carbohydrate donor is identical to the carbohydrate donor except for the fact that the precursor lacks an oxo group on its C-6 carbon. In a preferred mode the oxidation is achieved using a glycosyloxidase, e.g., galactose oxidase. Any leaving group compatible with the transglycosylation reaction may be employed. However, preferred leaving groups on the carbohydrate donor are selected from a group consisting of radicals represented by the following structures:

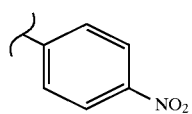 and 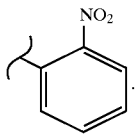

Preferred carbohydrate donors may be selected from a group consisting of molecules represented by the following structures:

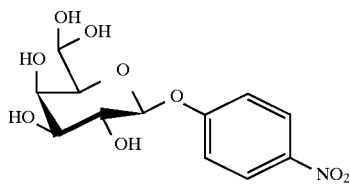

and

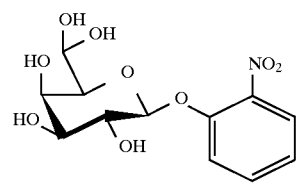

Preferred precursor carbohydrate donors may be selected from a group consisting of molecules represented by the following structures:

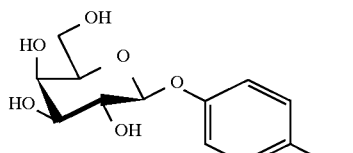

and

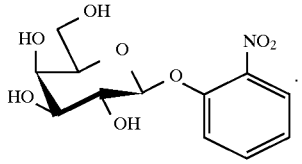

In a preferred mode, the transglycosylation reaction is catalyzed with a molar excess of the second galactosidase substrate as compared to the first galactosidase substrate. A five fold or greater molar excess may be employed. However, a ten fold molar excess is preferred. Preferred carbohydrate acceptors include N-acetyl-D glucosamine and N-acetyl-D glucosamine glycoside.

If a non-oxidized transglycosylation product is desired, then the C-6 oxo group of the transglycosylation product may be reduced using a reducing agent for producing the non-oxidized transglycosylation product having a single C-6 hydroxyl group. A preferred reducing agent is sodium borohydride. After the reduction step, non-oxidized transglycosylation product may be separated from the second galactosidase substrate glycosyl acceptor for producing a purified non-oxidized transglycosylation product. A preferred mode of purified non-oxidized transglycosylation product is N-acetyl-D-lactosamine.

A preferred unreduced transglycosylation product is represented by the following formula:

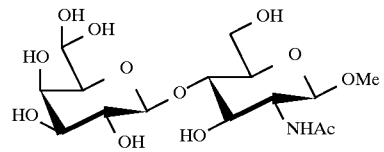

DESCRIPTION OF FIGURES

FIG. 1 illustrates β-Galactosidase-catalyzed transglycosylation and hydrolysis. (a) Use of substrate with poor leaving group (e.g. Galβ1,4Glc) and with good leaving group (b). E represents β-galactosidase.

FIG. 2 illustrates the comparison of β-galactosidase-catalyzed reaction using galactopyranose (GalβOpNP) and galactohexodialdose (6-oxo-GalβOpNP). (a): The reaction mixture containing 0.05M of donor, and various concentrations of N-acetyl-D-glucosamine in 0.05M potassium phosphate buffer (pH 7.0) was gently stirred at room temperature in the presence of the enzyme (140 U/mmol of donor) for 24 hours; (b) The mixture (containing the same components as described in (a)) was incubated with shaking for 5–10 min at room temperature. Absorbance was measured at 420 nm; (C) Methyl-β-N-acetyl-D-lactosamine (5) was obtained by reduction with NaBH$_4$ followed by product isolation.

DETAILED DESCRIPTION OF THE INVENTION

Figure 3:
FIG. 3 illustrates synthesis of lactosamine 5 using galactose oxidase (GO) and β-galactosidase from *B. circulans* with the indicated steps, starting from p-nitrophenyl galactoside (1, GalβOpNP).

The invention is directed to the chemoenzymatic preparation of N-acetyl-D-lactosamine (Galβ1,4GlcNAc, LacNAc) by tandem use of Galactose Oxidase and β-Galactosidase using the p-nitrophenyl glycoside of D-galactohexodialdose (6-oxo-GalβOpNP) as donor.

FIG. 1 shows the reactions catalyzed by β-galactosidase. As reported, (Hedbys et al. *Carbohydr. Res.* 1989, 186, 217–223), the use of substrate with poor leaving group (e.g. lactose) as a glycosyl donor often gave a complex mixture of products including mono, di and trisaccharides. The use of substrate with good leaving group (such as p-nitrophenyl galactoside) and an excess of glycosyl acceptor would make the reactions irreversible and minimize the secondary hydrolysis and further glycosylation of the transglycosyl product, the hydrolysis product and the donor itself.

In order to determine which step is kinetically controlled, the effect of acceptors on initial reaction rate, $(V)_0$, was investigated (FIG. 2). In the case of p-nitrophenyl galactoside (1, GalβOpNP), the initial reaction rate measured by the released p-nitrophenol did not increase with the addition of acceptor (entries 1–3), though the transglycosylation yield increased from 14% to 30%. These results suggest that the rate determining step is perhaps the formation of (E-S) complex and the ratio between transglycosylation and hydrolysis mainly depends on the concentrations of acceptor and $H_2O$. In aqueous solution, hydrolysis is therefore the major pathway. Addition of water soluble organic solvent would reduce water activity to some extent, but it often causes substrate and/or product inhibition and makes the enzyme unstable (Kieboom et al., *Recl. Trav. Chim. Pays-Bas* 1988, 107, 347–348). To shift the reaction toward transglycosylation in water, it is therefore necessary to kinetically control the partitioning step to favor the transglycosylation.

When compound 1 was oxidized to the 6-oxo-derivative 2 (Bretting et al. *Biochim. Biophys. Acta* 1987, 913, 342–348), it was found to be a relatively weak substrate for β-galactosidase. The initial rate and transglycosylation yield, however, increased with increase of the acceptor 3 (FIG. 2; entries 4–6). This result indicates that the active species generated from 2 is less reactive with water than with the acceptor 3.

Another problem in β-galactosidase-catalyzed reactions is that the product is also subject to the enzymatic hydrolysis. The improved stability of 6'-oxo-LacNAc (4, $T_{1/2}$=31 h) compared to 2 ($T_{1/2}$=0.4 h) toward the β-galactosidase-catalyzed hydrolysis may also contribute to the high yield of the product.

The half-lives of compounds 2 and 4 determined from the pseudo first order kinetics of the β-galactosidase-catalyzed hydrolysis were measured as below. 2: A 0.5-mL solution of potassium phosphate buffer (50 mM, pH 7.0) containing 2 (5 mM) and β-galactosidase (140 unit per 1 mmol of 2) was measured continuously in a plastic cell with a 1 cm light path at 420 nm against a control in the absence of the enzyme. 4: A 5-mM solution of 4 and the enzyme (140 U/mmol) in $D_2O$ was poured into an NMR tube, the ratio between the released 3 and remaining 4 was determined periodically by the integration of 6-H of 4 (3.98 ppm) and 6-H of 3 (3.88 ppm).

Although the transgalactosylation reaction of 2 proceeded nicely with excellent regioselectivity and good yield under the reaction condition, use of excess amounts of acceptor may complicate product purification. The aldehyde produced, however, may be reduced with $NaBH_4$ in non-aqueous solution to form a boron complex which would be decomposed by addition of water to give the desired alcohol (FIG. 3).

Figure 4:
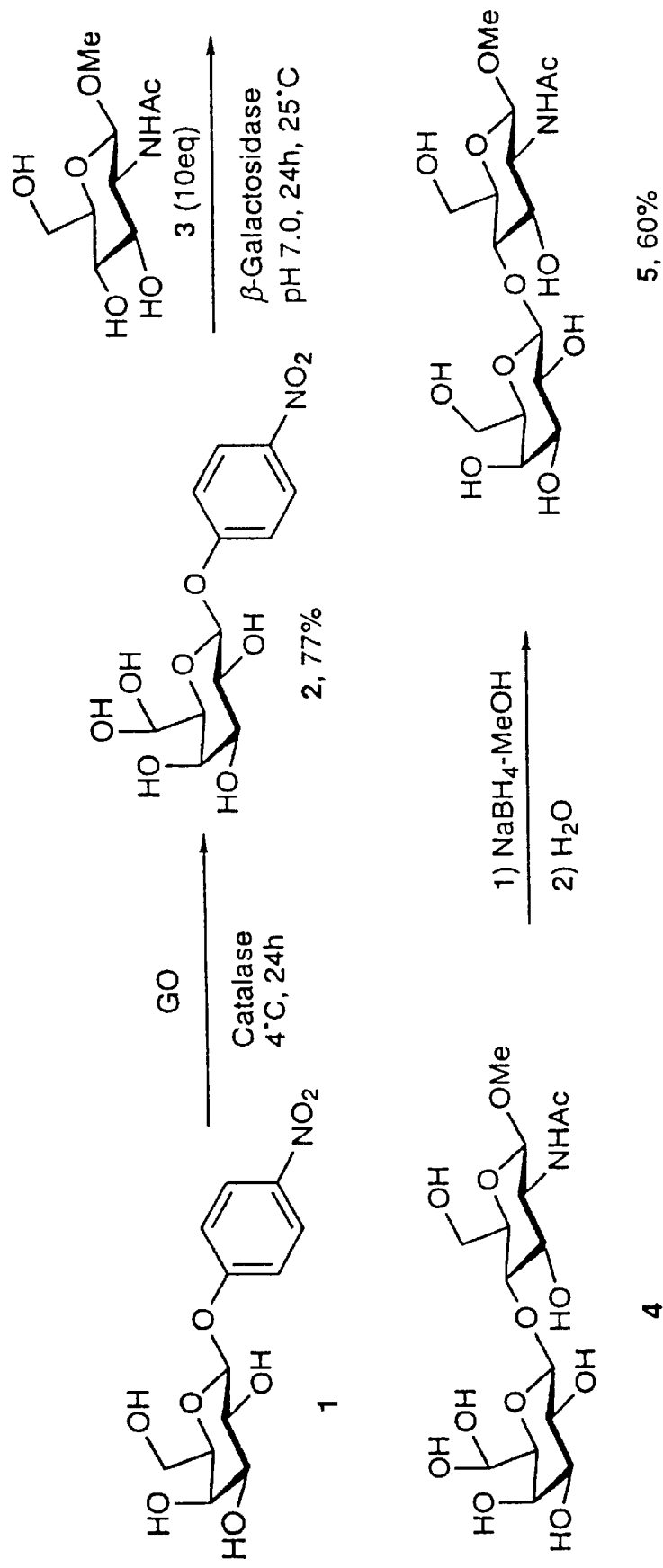
FIG. 4 illustrates that the p-nitrophenyl glycoside of D-galactohexodialdose, derived from oxidation of the galactose derivative with galactose oxidase, was used as a novel donor in transglycosylation reaction catalyzed by β-galactosidase from *Bacillus circulans*. Acceleration of the initial reaction rate by adding an excess of acceptor and the improved stability of the product against enzymatic hydrolysis resulted in the production of 6-oxo-N-acetyl-D-lactosamine in high yield. Reduction of the enzymatic reaction mixture with $NaBH_4$ in MeOH followed by simple purification effectively removed excess amounts of N-acetyl-D-glucosamine to obtain N-acetyl-D-lactosamine in 60% yield.

To test the feasibility of the above approach, a mixture of 3 and 4 obtained from the enzymatic reaction was reduced with $NaBH_4$ in MeOH. When the reaction was terminated, the reaction mixture was separated by silica gel column chromatography. First, 3 was eluted with non-aqueous solvent ($CHCl_3$—MeOH 1:1) and was recovered in 77%. Compound 5 was next eluted with aqueous solvent ($CHCl_3$—MeOH—$H_2O$ 5:5:1) and was obtained in 60% yield. The recovered compound 3 could be reused in the next cycle of the reaction without further purification (FIGS. 3 and 4 steps 1 and 2).

In summary, a new method based on galactosidase has been invented for synthesis of β-galactoside, using 6-oxo-Galβ-galactoside using 6-oxo-GalβOpNP as donor. This method can be carried out in aqueous solution without organic solvent to give the transglycosylation product in high yield and high regioselectivity.

EXPERIMENTAL PROTOCOLS

General A Bruker AMX-400 spectrometer was used for 400 MHZ $^1H$ NMR and 100 MHZ $^{13}C$ NMR spectra. High resolution mass spectra (HRMS) were obtained on a VG ZAB-ZSE Mass Spectrometer in fast atom bombardment. For the MS of the compounds that are obtained from the MCC, normal molecular ion peaks ($M+H^+$, $M+Na^+$ or $M+Cs^+$) were recorded without high resolution.

Water was distilled from Milli-Q water system in Millipore. Chemicals and solvents were reagent grade and were used without further purification. 4-Nitrophenyl-β-D-galactopyranoside is available from Aldrich. Ion-exchange resin (Dowex 1X8, $Cl^-$ from, 100–200 mesh) was obtained from Sigma. Biogel P-2 was obtained from Sigma. Analytical thin-layer chromatography was performed with pre-coated Merck silica gel type 60, $F_{254}$.

The following enzymes were obtained from Sigma: galactose oxidase, catalase and β-galactosidase. Commercial enzymes were not assayed; the reported activities refer to the activities stated by Sigma.

The enzyme-catalyzed reactions were performed in teflon tube under argon at ca. 25° C. (or otherwise indicated in protocol). Oxygen was removed from the solution before use by bubbling a stream of argon through the stirred solution for 30–45 min.

The galactosidase substrates p-nitrophenyl galactoside (1, GalβOpNP) and o-nitrophenyl galactoside (GalβOoNP) were obtained from Sigma or Aldrich.

Synthesis of Compound 2

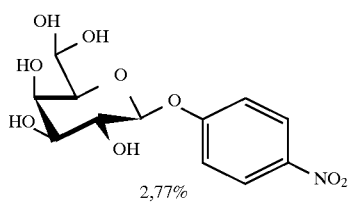

2, 77%

Compound 2: To a solution of 1 (306 mg, 1.02 mmol) in 50 mM potassium phosphate buffer (pH 7.0, 15 mL) was added galactose oxidase (135 U; Sigma) and catalase (1 mg; Sigma). The reaction mixture was gently stirred under oxygen balloon for 24 hours at 4° C. After MeOH was added to terminate the reaction, the solvent was removed in vacuo. The residue was applied on silica gel column chromatography ($CHCl_3$ then $CHCl_3$:MeOH= 1:1) to obtain 2 (250 mg, 77%). $^1$H NMR (500 MHZ, $D_2O$): δ 3.64 (1H, dd, J=7.5, 1.0), 3.79 (1H, dd, J=9.5, 3.0), 3.88 (1H, dd, J=10.0, 7.5), 4.17 (1H, d, J=2.5), 5.13 (1H, d, J=7.5), 5.19 (1H, d, J=7.5), 7.26 (2H, d, J=7.0), 8.27 (2H, d, J=7.0).

Synthesis of Compound 4

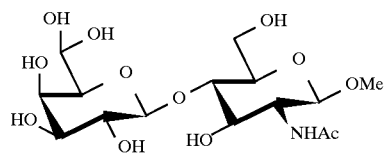

To prepare 4 as an authentic sample, compound 5 was oxidized by galactose oxidase (Sigma) under the same condition as that described for the synthesis of 2 except that $CuSO_4$ (0.5 mM) was added and the product was purified by Biogel P-2.

Compound 4: $^1$H NMR (500 MHZ, $D_2O$): δ 2.02 (3H, s), 3.45 (1H, d, J=7.5), 3.50 (3H, s), 3.55 (1H, dd, J=10.0, 8.0), 3.57–3.63 (1H, m), 3.66 (1H, dd, J=10.0, 3.5), 3.67–3.74 (3H, m), 3.82 (1H, dd, J=12.5, 5.5), 3.98 (1H, d, J=12.5, 1.5), 4.07 (1H, d, J=3.0), 4.45 (1H, d, J=8.0), 4.47 (1H, d, J=8.0), 5.12 (1H, d, J=7.5). HRMS calcd for $C_{15}H_{25}NO_{11}Na$ (M+Na, aldehyde form) 418.1325, found 418.1310.

Synthesis of Compound 5

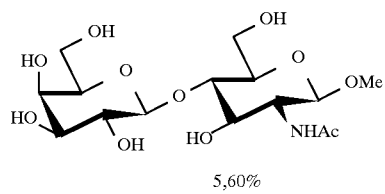

5, 60%

Compound 5. To a solution of 3 (181 mg, 770 mmol) and β-galactosidase (11 U; Sigma) from *Baccilus circulans* in 50 mM potassium phosphate buffer (pH 7.0, 1.54 mL) was added 2 (24.4 mg, 77.0 mmol). The reaction mixture was gently stirred for 24 hours at room temperature. After addition of MeOH (1 mL) to terminate the reaction, the solvent was thoroughly removed in vacuo. The residue was dissolved with MeOH (5 mL) and $NaBH_4$ (29 mg) was added to the solution at 0° C. After stirring for 1 hour at 0° C., the mixture was allowed to rise to room temperature within 10 hours. The residue was applied to silica gel column chromatography and at first eluted with 500 mL of a mixture of $CHCl_3$ and MeOH (1:1) to recover 3 (140.1 mg, recovery yield 77% for staring amount). Then the eluting solvent was changed to a mixture of $CHCl_3$:MeOH:$H_2O$ (5:5:1) to obtain 5 (18.2 mg, 60%).

What is claimed is:

1. An improved process for producing a β-galactoside transglycosylation product, the process employing a β-galactosidase for catalyzing a transglycosylation reaction between a first β-galactosidase substrate and a second β-galactosidase substrate for producing the β-galactoside transglycosylation product, the first β-galactosidase substrate being a glycosyl donor having an anomeric carbon and a C-6 carbon, the anomeric carbon having a glycosidic leaving group attached thereto, the second β-galactosidase substrate being a glycosyl acceptor, wherein the improvement is characterized as follows:

the C-6 carbon of the glycosyl donor having an oxo group attached thereto.

2. An improved process for producing a β-galactoside transglycosylation product as described in claim 1 comprising the following additional step:

prior to said catalyzation of the transglycosylation reaction, oxidizing a precursor glycosyl donor having the C-6 carbon for providing the glycosyl donor with the oxo group attached to the C-6 carbon.

3. An improved process for producing a β-galactoside transglycosylation product as described in claim 2 wherein said oxidation step is catalyzed by a glycosyloxidase.

4. An improved process for producing a β-galactoside transglycosylation product as described in claim 3 wherein the oxidase is galactose oxidase.

5. An improved process for producing a β-galactoside transglycosylation product as described in claim 1 wherein said leaving group is selected from a group consisting of radicals represented by the following structures:

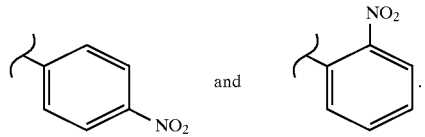

6. An improved process for producing a β-galactoside transglycosylation product as described in claim 5 wherein the glycosyl donor is selected from a group consisting of molecules represented by the following structures:

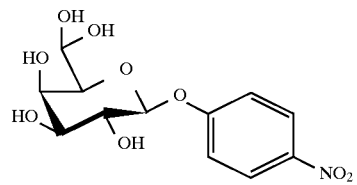

and

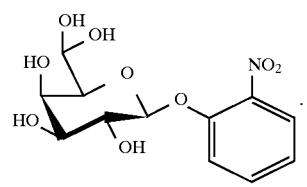

7. An improved process for producing a β-galactoside transglycosylation product as described in claim 2 wherein the precursor glycosyl donor is selected from a group consisting of molecules represented by the following structures:

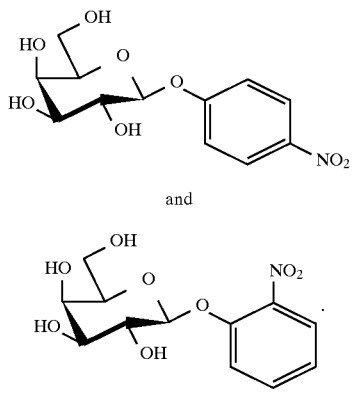

and

8. An improved process for producing a β-galactoside transglycosylation product as described in claim 1 wherein said catalyzation of the transglycosylation reaction is performed with a five fold or greater molar excess of the second β-galactosidase substrate as compared to the first β-galactosidase substrate.

9. An improved process for producing a β-galactoside transglycosylation product as described in claim 1 wherein the carbohydrate acceptor is selected from the group consisting of N-acetyl-D glucosamine and N-acetyl-D glucosamine glycoside.

10. An improved process for producing a β-galactoside transglycosylation product as described in claim 1 wherein the β-galactoside transglycosylation product includes a C-6 oxo group and comprises the following additional step:

after said catalyzation of the transglycosylation reaction, reducing the C-6 oxo group of the β-galactoside transglycosylation product using a reducing agent for producing a non-oxidized transglycosylation product having a single C-6 hydroxyl group.

11. An improved process for producing a β-galactoside transglycosylation product as described in in claim 10 wherein said reducing agent is sodium borohydride.

12. An improved process for producing a β-galactoside transglycosylation product as described in claim 10 comprising the following additional step:

after said reduction step, separating the non-oxidized transglycosylation product from the second β-galactosidase substrate glycosyl acceptor for producing a purified non-oxidized transglycosylation product.

13. An improved process for producing a β-galactoside transglycosylation product as described in claim 12 wherein said separation step is performed using silica gel column chromatography.

14. An improved process for producing a β-galactoside transglycosylation product as described in claim 12 wherein the purified non-oxidized transglycosylation product is N-acetyl-D-lactosamine.

* * * * *